US005705273A

United States Patent [19]

Denry et al.

[11] Patent Number: 5,705,273
[45] Date of Patent: Jan. 6, 1998

[54] METHOD FOR STRENGTHENING DENTAL RESTORATIVE MATERIALS

[75] Inventors: Isabelle L. Denry; Stephen F. Rosenstiel, both of Columbus, Ohio

[73] Assignee: The Ohio State University, Columbus, Ohio

[21] Appl. No.: 400,362

[22] Filed: Mar. 8, 1995

[51] Int. Cl.[6] .................. B32B 17/00; C03C 17/00; B05D 3/02; B05D 3/10
[52] U.S. Cl. .................. 428/410; 427/2.27; 427/2.29; 427/380; 427/419.1; 65/30.13; 65/30.14
[58] Field of Search ............... 427/2.26, 2.27, 427/2.29, 380, 419.1; 106/35; 428/410; 65/30.14, 30.13; 433/8

[56] References Cited

U.S. PATENT DOCUMENTS

| | | | |
|---|---|---|---|
| 2,779,136 | 1/1957 | Hood et al. | 428/410 |
| 3,395,998 | 8/1968 | Olcott | 65/30.14 |
| 3,630,704 | 12/1971 | Garfinkel et al. | 65/30.14 |
| 3,751,238 | 8/1973 | Grego et al. | 65/30.14 |
| 3,765,855 | 10/1973 | Larrick | 65/30.14 |
| 3,798,013 | 3/1974 | Inoue et al. | 65/30.14 |
| 3,853,674 | 12/1974 | Levene | 427/399 |
| 3,879,274 | 4/1975 | Matsumori et al. | 65/30.13 |
| 4,206,253 | 6/1980 | Watanabe | 427/422 |
| 4,483,700 | 11/1984 | Forker, Jr. et al. | 65/30.14 |
| 4,546,006 | 10/1985 | Ohno et al. | 106/35 |
| 4,550,030 | 10/1985 | Ohi et al. | 427/2 |
| 4,702,760 | 10/1987 | Garcia de Leon | 427/479 |
| 4,784,606 | 11/1988 | Jones et al. | 501/7 |
| 4,798,536 | 1/1989 | Katz | 433/212.1 |
| 4,872,896 | 10/1989 | LaCourse et al. | 65/30.14 |
| 5,071,801 | 12/1991 | Bedard et al. | 501/128 |
| 5,077,132 | 12/1991 | Maruno et al. | 427/380 |
| 5,453,290 | 9/1995 | van der Zel | 427/2.26 |

OTHER PUBLICATIONS

Crimaldi, A.J. et al., "Strengthening of Leucite–reinforced Porcelain by Double Ion Exchange." General Session and Exhibition of the International Association for Dental Research, Poster Session, Thursday, Mar. 10, 1994.

Denry, I.L. et al., "Enhanced Chemical Strengthening of Feldspathic Dental Porcelain." *Journal of Dental Research*, vol.72, No. 10(Oct. 1993), pp. 1429–1433.

Dunn, B. et al., "Improving the Fracture Resistance of Dental Ceramic." *Journal of Dental Research*, vol. 56, No. 10,(Oct. 1977), pp. 1209–1213.

Nordberg, M.E., et al., "Strengthening by Ion Exchange." *Journal of the American Ceramic Society*, vol. 47, No. 5(1964), pp. 215–219, (no month).

Vaidyanathan, T.K., et al., "Properties of a New Dental Porcelain." *Scanning Microscopy*, vol. 3, No. 4(1989), pp. 1023–1033, (no month).

Varshneya, Arun K. et al., "Technology of Ion Exchange Strengthening of Glass: A Review." in Varshneya A.K., et al *Fusion and Processing of Glass* (Westerville, Ohio, American Ceramic Society, 1993), pp. 365–376, (no month).

*Primary Examiner*—Diana Dudash
*Attorney, Agent, or Firm*—Philip J. Pollick

[57] ABSTRACT

A method for strengthening and increasing the thickness of the strengthened surface layer of a dental ceramic restorative material where the ceramic material is heat treated with a salt composition containing a lithium ion and a metal ion larger than the lithium ion first at a temperature above the strain temperature followed by a second heat treatment with the salt composition at a temperature below the strain temperature. The treatment is especially effective for all-ceramic, high-leucite feldspathic porcelain restorations.

25 Claims, No Drawings

METHOD FOR STRENGTHENING DENTAL RESTORATIVE MATERIALS

BACKGROUND OF THE INVENTION

1. Field of the Invention

This invention relates to a method for strengthening dental ceramics such as glasses and porcelains. More particularly it relates to increasing both the strength and thickness of the strengthened surface layer of dental ceramics and especially those ceramics used for all-ceramic dental restorations such as feldspathic porcelains containing leucite.

2. Background Description

Some of the earliest dental restorations were carved from ivory and walrus tusks. About two-hundred years ago, Dubois du Chemant developed the first method for the fabrication of porcelain teeth which subsequently led to the production of denture teeth on a commercial basis in the United States and England by about 1840. Land patented the porcelain jacket crown in 1899 and the porcelain inlay followed some years later.

The porcelains are particularly suitable for dental restorative applications in that these materials are quite inert to the various foods and drinks likely to be consumed by the individual in whom the restoration is placed. Furthermore, they have a high biological acceptance by their host even after many years of continuous use. Because porcelains can be colored to match closely the teeth with which they are used, they have acquired prominence as being one of the most aesthetically desirable dental restorative materials. All of these factors have contributed to making dental porcelains one of the most important materials used in dentistry.

Porcelain dental restorative materials do, however, have one great disadvantage—they are relatively fragile and often break when subjected to severe external forces such as can be established during, for example, mastication. Such breakage can often be traced to the presence of numerous flaws including submicroscopic cracks and defects (Griffith flaws) on the surface of the material. These flaws can act as stress concentrators when the object is subjected to external forces and the microscopic stress occurring at tip (bottom) of the flaw is the direct cause of fracture when the critical breaking stress is reached.

One of the first approaches to the problem of the fragility of porcelain restorations was the use of a metallic framework to support and alleviate some or all of the stress on the porcelain restoration. Because the porcelain was fused to the metallic dental alloy framework, one of the initial problems with this approach was that differences in the coefficient of expansion of the metal alloy and the porcelain resulted in excessive stress formation during cooling from the high-temperature processing required to fuse the porcelain and metallic alloy. To overcome the problem of mismatched coefficients of expansion, Weinstein et al (U.S. Pat. Nos. 3,052,982 and 3,052,983) produced a dental porcelain from two different frits, one having a low coefficient of expansion and the other having a high coefficient of expansion. The resulting mixed porcelain had a coefficient of expansion intermediate between the two materials. By adjusting the proportions of the two materials, a porcelain could be obtained that had a coefficient of expansion that matched the dental alloy used as the support. One major problem still remained with the metal/porcelain restoration—a noticeable loss of translucency of the porcelain in that portion of the restoration where it is backed by the metal alloy.

Another approach to the reduction of the fragility of porcelain restorations has been the addition of a crystalline reinforcement material to the porcelain matrix. The crystalline structures are typically stronger than the noncrystalline matrix as a result of the maximum packing density of the atoms forming the crystalline state. Initially these materials used an aluminous composition (crystalline alumina) as the strengthening reinforcement material. In order to overcome the reduced translucency produced by the alumina, Katz (U.S. Pat. No. 4,798,536) produced a feldspathic porcelain composition with a crystalline leucite content of more than forty-five percent leucite in the glassy matrix.

The final method of reducing dental ceramic fragility has been through the use of surface strengthening techniques. These techniques involve two basic methodologies, 1) physical strengthening, based on thermal treatment and 2) chemical strengthening based on chemical changes in the surface composition of the porcelain material. Thermal (heat) treatment typically involves the rapid cooling of the surface portion of the treated material. This rapid cooling causes the surface layer to contract and compress as a result of the relatively unchanged (uncontracted) hot inner material. This compressed material reduces the tendency for the material to form microscopic defects and cracks (Griffith flaws). As the inner (bulk) material subsequently cools, tension is produced between the compressed surface layer and the bulk material. If the surface layer is not sufficiently thick, the tensile (pulling) forces produced by the subsequent cooling of the bulk (inner) material may cause breakage of the compressed surface layer. That is, the pulling (tensile) forces produced by the cooled inner material pull the compressed outer layer inward so strongly that the outer layer cracks. Although such breakage can be reduced by annealing techniques in which the entire material is reheated to a temperature below the glass transition temperature ($T_g$; the temperature at which a material changes from a plastic to a brittle state), this involves additional processing steps. Moreover, in addition to one or more subsequent annealing steps, the initial heating and cooling steps must be carefully controlled to insure that a minimum thickness of the surface layer is achieved. In addition, the shape of the restoration may make it impossible to obtain a sufficiently uniform stress distribution for dental applications.

The second technique for surface strengthening involves chemical modification of the surface layer of the restoration material to produce a compressed surface layer, that is, a surface layer under compressive forces. This can be accomplished by the replacement of smaller ions such as sodium with large ions such as potassium at a temperature below the glass transition temperature, Tg. Ohi et al (U.S. Pat. No. 4,550,030) have found that by coating a dental restorative ceramic that is fused to a metal support material with one or more large inorganic rubidium, cesium or potassium salts and heating the coated restorative material to a temperature that is both below the melting point of the salts and also below the strain temperature (similar to the glass transition temperature, $T_g$, but defined as the temperature at which the material has a viscosity of $10^{14.6}$ Poise), the surface of the restorative material can be strengthened. These large ions "push" against the surrounding material to compress it to prevent fracture from occurring at the Griffith flaws. However, the shallow depth of ion-exchange penetration and the moderate strengthening are not sufficient to enable an all-ceramic restoration to withstand the surface abrasion experienced over the expected lifetime of such restorations. That is, a small microscopic nick or chip in the surface of the restoration that extends below the treated layer puts the restoration at risk of cracking in a fashion similar to that of an untreated restoration.

Denry et al (*Journal of Dental Research*, Vol 72 (10) pp. 1429–1433 (1993)) have demonstrated the use of a similar technique that involves an additional ion exchange step, that is, a double ion exchange. In the Denry method, lithium ion was first exchanged with a dental ceramic at a temperature above the stain temperature. This is followed by a second step in which potassium ion was exchanged with the ceramic at a temperature below the strain temperature using the Ohi et al method. The resulting ceramic showed only a small increase in the layer thickness and amount of strengthening (a 5 micron increase in layer thickness and a 23% increase in strength over the Ohi et al method). The overall results were insufficient to provide a layer depth and strength necessary to significantly extend the life of a dental ceramic, especially when the ceramic is used without a metal support, that is, as an all-ceramic restoration.

Consequently, the all-ceramic dental restoration remains subject to a shortened lifetime as a result of cracking susceptibility. The development of a method for strengthening, that is, improving the thickness and durability of the surface layer of dental ceramic restorations remains a heartfelt and unsolved need in the area of restorative dentistry.

Accordingly, it is an object of this invention to provide a method for producing a thicker surface strengthened layer on ceramic dental restorations.

It is an object of this invention to provide a method for further strengthening the surface layer on dental restorative materials.

It is an object of the present invention to provide a method of strengthening the surface layer of dental restorative materials that can be accomplished with a single heating step.

It is an object of the present invention to provide a method of strengthening the surface layer of dental restorative materials that minimizes the loss of translucency and color of the restorative material.

It is an object of the present invention to provide a method of strengthening the surface layer of ceramic dental restorative materials using conventional dental equipment.

It is a further object of the present invention to provide a method of strengthening restorative dental materials using readily available chemical reagents.

SUMMARY OF THE INVENTION

In order to meet these objects, this invention features a method for strengthening and increasing the thickness of the strengthened surface layer of a dental ceramic restorative material where the ceramic material is heat treated with a salt composition containing a lithium ion and a metal ion larger than the lithium ion first at a temperature above the strain temperature followed by a second heat treatment at a temperature below the strain temperature. The treatment is especially advantageous in that it affords a longer lasting all-ceramic dental restoration with superior strength and durability not heretofore achieved. The method is also useful in improving the durability and strength of a wide variety of ceramics and metal supported restorations including high and low content leucite feldspathic ceramics, aluminosilicates, and feldspathic porcelains.

The method features inexpensive and readily available reagents such as the alkali metal halides, sulfates, nitrates and phosphates such as sodium and potassium chloride. Although the inorganic lithium/alkali metal salt mixtures is not required for the low temperature heat treatment, its use significantly improves the strength and durability of the ceramic. Of particular advantage is the fact that the high and low temperature heat treatments can be carried out with the same lithium/metal salt composition thereby eliminating addition processing steps.

It is contemplated that variations in procedures, structural requirements and arrangement of materials may appear to a person skilled in the art without departing from the scope of or sacrificing any of the advantages of the invention.

DETAILED DESCRIPTION OF THE INVENTION AND BEST MODE FOR CARRYING OUT THE PREFERRED EMBODIMENT

The method of the present invention is directed to both further strengthening and extending the depth of the compressive surface layer of a restorative dental ceramic. The method features the use of a mixture of inorganic salts having a small and a large cation in a heat treatment step carried out above the strain temperature. The use of the salt mixture in a high-temperature heat treating step has the advantage of significantly improving the strength, depth, and durability of the ceramic surface layer. The method is carried out by depositing a mixture of an inorganic lithium salt and an inorganic metal salt with a metal ion larger than the lithium ion of the lithium salt on the ceramic. The ceramic with its deposited salt mixture is heat treated at a temperature above the strain temperature. This is followed by a second heat treatment at below the strain temperature. The resulting heat-treated ceramic shows a significant increase in strength and a substantially thicker compressive surface layer.

As used here, dental ceramic is used in its conventional sense as applied to both glasses and fritted materials—glasses typically being shaped after heating while fritted materials are first heated, then quenched and ground to a powder (frit) which is then shaped and subsequently heated (fired) to produce the final product. It is to be realized that the fritted powder can also be heated and shaped after or during the final heating.

The method of the present invention is especially applicable to dental ceramics containing aluminous and aluminosilicate components. This includes aluminosilicate glasses and fritted materials such as porcelains which include feldspar-based materials and especially feldspathic porcelains that contain at least about thirty percent leucite, leucite being a crystalline material known to significantly strengthen the restoration. At about thirty percent leucite, the dental ceramic achieves sufficient strength to be suitable for all-ceramic restorations. The present method is especially attractive in that it allows these high-strength leucite materials to take on an additional strength and durability necessary for an extended period of use. It is noted however, that the present material is not limited to these high-strength materials but may also be used with other dental ceramics such as those used with metal support structure.

Typical dental feldspathic porcelain powders consist of finely pulverized frits of potash feldspar orthoclase (potassium aluminosilicate, $KAlSi_2O_6$), soda feldspar albite (sodium aluminosilicate, $NaAlSi_2O_6$) and varying amounts of quartz (silica or silicon dioxide, $SiO_2$). Typically the frits are prepared by mixing various amounts of a native feldspar such as Wyoming feldspar that has been culled to remove impurities such as mica and quartz. Next the feldspar is ground to a fine powder of which about 95% passed through an, e.g., 180 mesh screen. A magnetic separator is used to remove any iron impurities. The powder is again milled (ground) and screened through a small sized, e.g., 200 mesh screen. A flux of typically water soluble materials such as lithium carbonate, calcium carbonate, potassium silicate, potassium nitrate, etc. is added so that the final composition of the after firing will have a appropriate feldspathic dental porcelain composition. The typical dental porcelain consists of about 50–70% silicon dioxide ($SiO_2$), 15–20% aluminum oxide ($Al_2O_3$), 12–23% potassium oxide ($K_2O$), and 2–7% sodium oxide ($Na_2O$) together with a varying amount of other trace elements such as lithium oxide ($Li_2O$), calcium oxide (CaO), magnesium oxide (MgO), and cerium oxide ($Ce_2O_3$). To form the leucite crystallites and insolubilize the various water soluble additives (flux), the ground powder is heated to about 1250° C. to from a glassy (vitreous) matrix with a uniform distribution of leucite crystals. The molten material is quenched by pouring into water, dried, crushed, and ground to a fine powder (frit) passing though, for example, a 200 mesh screen. Small amounts of pigments (chromates, vanadates, and manganates) and opacifiers (e.g., tin oxide) are added to give the appropriate dental shade. The powder is mixed with water and applied to an appropriate die to obtain the appropriate dental construction. The resulting composition in its desired form is dried and then fired at about 1050° C. to give the dental restoration. Further details as to the preparation of feldspathic dental restorations and especially those related to leucite strengthened restorations and surface strengthening compositions can be found in U.S. Pat. No. 4,798,536 and U.S. Pat. No. 4,550,030 all of which are herein incorporated by reference as if completely written herein.

A feldspathic dental composition containing leucite crystals has a random, glass-type matrix composed of potassium aluminosilicate ($K_2O.Al_2O_3.6SiO_2$) and typically includes sodium ions ($Na^+$) and may contain other positive ions (cations) such as lithium ($Li^+$) and calcium ($Ca^{2+}$) in which small crystallites of leucite are distributed. Leucite is a crystalline potassium aluminum silicate similar in composition to the feldspathic matrix composition but being crystalline and having the formula $K_2O.Al_2O_3.4SiO_2$. Leucite may also exist as a mixture of potassium and sodium ions, that is, have a formula of $K_{1-x}Na_xAlSi_2O_6$. A wide variety of feldspar based ceramic materials are used for dental restoration, all of which may benefit from the process of this invention. Such materials, their formulations, and preparation are well known in the art. Preferably, however, this strengthening treatment is especially useful with high-leucite containing (above about 30 wt. % leucite) feldspathic dental porcelain restoration materials such as described in the U.S. Pat. No. 4,798,536 where such treatment allows for a greater life of all-ceramic dental restorations. Typically the ceramic restoration is prepared and fired to its final state according to manufacturer's instruction prior to treatment with the process of the present invention.

In the first step of the process, a mixture of inorganic salts is applied to the surface of the ceramic material that is to be surface strengthened. One of the salts is a lithium salt such as a lithium halide, sulfate, nitrate, lithium carbonate, or lithium phosphate. The second salt of the mixture is a metal salt with a metal having an ionic radius that is significantly larger than the lithium ionic radius. Preferably the metal ion should have a radius that is at least 25% larger than the lithium ionic radius. More preferably, the metal ion has an ionic radius that is at least 50% larger than the lithium ionic radius.

Preferably the metal ion is an alkali metal ion other than lithium, that is, sodium, potassium, rubidium, or cesium. Francium could also be used but its radioactivity prevents its use in the biological environment in which the ceramic restoration is placed. More preferably, the metal ion is sodium or potassium. In choosing the metal ion, it should be realized that too great a difference between the lithium and metal ion may be detrimental to the process since an ion with too large a radius may be significantly retarded in its penetration into the surface layer.

Typical inorganic metal salts for use with this invention include alkali metal halides, carbonates, sulfates, nitrates, and phosphates. In selecting the lithium and metal salts, salts should be selected that are molten above the strain temperature and which are solid below the strain temperature of the ceramic material being treated. It must also be remembered that since a mixture of salts is being used, the mixture is likely to form a eutectic with a lower melting point than either of the component salts. For a ceramic having a strain temperature of about 555° C., lithium chloride and sodium or potassium chloride gives a suitable treatment mixture.

In determining the ratio of lithium and metal salts, it has been found that the ratio is dependent on the composition of the ceramic material to be treated. Thus for a ceramic composition that already contains lithium ions in its glassy matrix, only a small amount of lithium salt is necessary while for a ceramic containing little or no lithium ion, a greater concentration of lithium ion is required. Thus for a high leucite (about 48%) feldspathic ceramic with about two percent lithium in the glassy matrix, a 1:9 mole ratio of Li:Na gave good strengthening results while for a low leucite (about 22%) ceramic having little or no lithium ion in the glassy matrix, a 1:1 mole ratio of Li:K gave a significant increase in strength.

To prepare the inorganic salt treatment mixture, the salts are typically mixed with a small amount of water to form a thick syrupy paste or slurry. The paste is applied to the fired (glazed) surface of the dental ceramic and allowed to dry giving a resulting mixture that is about 1.5 mm thick. The method of applying the salt mixture to the ceramic is not critical and a variety of ways, conventional in the art may be used. For example, salt mixture may be applied by dissolving it in water and spraying the solution on the ceramic. Organic binders such as gum arabic may be added to the mixture to facilitate the application process. If necessary, the ceramic is heated to remove solvents, dispersing agents and any binders prior to the treatment step. Alternatively the ceramic may be heat treated by placing it in a bath of the molten salt mixture at the appropriate heat treatment temperature.

After coating the ceramic with the salt mixture, it is heated to a temperature above the strain point in a burnout oven at a heating rate of about 5° C./min and held at this temperature for a period of time. As used here, the strain point or temperature is defined as the point when the ceramic material has a viscosity of $10^{14.6}$ Poise and may be approximated for the purposes of this invention as the glass transition temperature, $T_g$.

In determining the temperature to which the ceramic and salts are to be heated, it is to be realized the strengthening process of the present invention is a diffusion-controlled process. As such, three variables interact to determine the strengthening effect and thickness of the strengthened layer: the concentration of the diffusing species, the temperature, and the time. For a ceramic strain point of about 550° C., it is preferable to heat the ceramic to a temperature about two hundred degrees centigrade above the strain temperature to give satisfactory results in about thirty minutes. Although not wishing to be bound by such explanation, it is believed that at the temperature above the strain point, the lithium ion exchanges for the sodium and potassium in the ceramic material and the surface layer structure undergoes a slight contraction to accommodate the smaller lithium ion. As such, temperatures above but close to the strain point may not facilitate such a contraction. Of course, higher temperatures facilitate ion diffusion and shorten the time of the heat treatment step. At a temperature of about 200° C. above the strain temperature, a heat treatment (dwell) time of about 30 minutes gives satisfactory results. Higher temperatures shorten the heat treatment time. However, it must be realized that too high a temperature may have deleterious effects on the entire process. For example, if the ceramic material is a high percentage leucite feldspathic porcelain ceramic, too high a temperature may result in a partial melting of the leucite crystals and loss of at least a portion of the crystallite structure on cooling. As such, the phase diagram of the ceramic material should also be considered in selecting the temperature at which the first (high temperature) heat treatment is performed. Other than the critical temperature, the treatment temperature itself is not critical but is selected to carry out the process in a reasonable amount of time. As the treatment temperature approaches the strain point, the periods of time of ion exchange become significantly long, while at too high a temperature, negative effects such as a change in basic composition of the ceramic may be experienced. A temperature at least one hundred degrees and preferably about two hundred degrees above the stain temperature is appropriate for obtaining good strengthening results in a relatively short period. At about 200 degrees centigrade above the strain point, significant strengthening is obtained in about half an hour.

After the initial heat treatment at a temperature above the strain point, the temperature is lowered to a temperature below the strain point. Typically this is done by opening the oven door and allowing the ceramic to cool at a rate of about 1°/min. Clearly too slow a cooling rate in passing through the strain temperature is to be avoided as this will allow viscous relaxation of the ceramic to take place resulting in a failure to achieve the compressive forces that strengthen the surface layer.

After the sample has cooled to below the strain temperature, it is held at a second temperature below the strain point for a second heat-treatment period. Typically this heat treatment step is carried out at about fifty degrees centigrade and preferably one hundred degrees below the strain point. Higher temperatures, that is, temperatures too close to the strain point, allow viscous relaxation to occur. That is, the ceramic material is able to adjust to the larger size of the incoming larger ions and the compression profile is modified with a maximum stress (compression) at some distance from the surface. Should this distance be greater than the microscopic flaws (Griffith flaws) at the surface of the ceramic, the benefit of the second ion-exchange treatment is lost. See, for example, Dunn et al., *Journal of Dental Research*, 56(10) pp. 1209–1213 (1977). Of course, a further lowering of the temperature below the strain point results in a longer diffusion time to achieve a maximum strengthening effect.

Although it is preferable to have the salt mixture in contact with the ceramic for both the high (above strain point) and low (below the strain point) temperature heat treatments, it has been found that the lower heat treatment does not require the presence of the salt mixture to achieve some strengthening. It is also noted that a sample can be cooled to room temperature, the previous salt mixture from the high-temperature (above the strain point) heat treatment) removed and a new mixture of salt applied. However, by using the two-temperature heat treatment with the same salt mixture in place for both, a substantial increase in strength and durability can be achieved without the necessity of additional cooling, heating and reapplication steps. In this regard, it is noted that the composition of the salt mixture changes slightly after each heat treatment because of the ion-exchange process, however, the overall concentration is little affected because of the large excess of salt mixture with which the process is carried out.

The following Examples and Comparative Examples are given to explain the invention in further detail.

EXAMPLES I THROUGH X

One hundred discs of leucite reinforced dental porcelain (OPTEC HSP) 16 mm in diameter and 1.5 mm thick were prepared using a cylindrical stainless steel mold and plunger in the following fashion. Approximately 0.8 g of ceramic powder supplied by the manufacturer (OPTEC HSP; Jeneric Pentron, Inc, with the following fired glassy matrix composition: Si, 33.0; Al, 7.0; Ce 0.7; Ca, 0.1; Na 3.0; K, 7.6; Li 2.0; O 48.6%) was wetted with two drops of modelling liquid (water/glycerol type composition supplied by manufacturer) and pressed in an hydraulic press to a pressure of 2500 psi. The specimens were then ground to a thickness of 1.3 mm starting with 120 grit and finishing with 400-grit abrasive paper, prior to being fired according to the manufacturer's schedule in an Ultra-Mat Model CDF furnace (Uniteck Corp, Monrovia, Calif.) (Idle Temp, 538° C.; entry time, 5.5 minutes; Heating rate 55°/min; Vacuum level 720 mm/Hg; High Temp., 1038° C.; Hold Time, 2 min; Removal Time 2.5 minutes).

The specimens were randomly divided into ten groups (each group having a sample size of ten, i.e., n=10) and subjected to various treatments as indicated in Table I and in Examples I through X.

The mean flexural strength $\sigma_m$ was determined using a biaxial flexure test with a ball-on-ring set-up. All testing was carried out in water at a cross-head speed of 0.5 mm/min using a universal testing machine (Instron Model 1362, Instron Corp. Canton, Mass.). The specimens were placed with the treated side in tension. The maximum radial and tangential stresses for a specimen under concentric load are equal and were calculated according to the following equation:

$$\sigma_m = \frac{3P(1+v)}{4\pi t^2} \left[ 1 + 2\ln(a/b) + \frac{(1-v)}{(1+v)} \left[ 1 - \frac{b^2}{2a^2} \right] \frac{a^2}{R^2} \right]$$

where P is the load, t is the disk thickness, a is the radius of the support circle, b is the radius of uniform loading at center (estimated as t/3), R is the disc radius, and v is Poisson's ration (assumed to be 0.25; Anusavice et al, *International Journal of Prosthodontics*, Vol 5, pp. 351–358 (1992). The means for each group were calculated and differences between groups tested for statistical significance with ANOVA (analysis of variance) and Tukey's multiple range test.

COMPARATIVE EXAMPLE I

One set of discs was left untreated and subjected to the biaxial flexure test. The results obtained are shown in Table I.

COMPARATIVE EXAMPLE II

A second set of discs was heat treated without application of the inorganic salt mixtures. The mean flexural strength was determined. The results obtained are shown in Table I.

9

COMPARATIVE EXAMPLE III

A third set of discs was treated with Tuf-Coat (G-C International, Tokyo, JP; see also Ohi et al, U.S. Pat. No. 4,550,030) according to manufacturer's directions. A slurry (syrup) of the Tuf-Coat product (potassium orthophosphate) was coated on the discs to a thickness of 1–2 mm. The discs were heated to a temperature of about 150° C. at a heating rate of about 5° C./sec in a Jelenko Accu-Therm II, 1000 burnout oven (Jelenko Dental Health Products, Armonk, N.Y.) and held at that temperature for about 20 minutes to dry the material after which they were then immediately heated to a temperature of 450° C. at a heating rate of 5° C./min. The discs were held at this temperature for thirty minutes after which they were cooled to room temperature at 5° C./min (by opening the oven door). The salts were then brushed off and the discs washed in distilled water. The discs were tested for flexural strength according to the above set forth method. The results obtained are shown in Table I.

EXAMPLE IV

Reagent grade materials from Aldrich Chemical Company (Milwaukee, Wis.) were measured and mixed with a small amount of water to provide a 1:1 mole ratio of lithium:sodium ions as a syrupy liquid. The syrup was painted on the discs and the discs allowed to dry. The dried samples were heated to an initial temperature of 750° C. at a heating rate of 5° C./min in a Jelenko burnout oven equipped with digital readout and held at that temperature for thirty minutes. The samples were then cooled by opening the oven door to a temperature of 450° C. (at a cooling rate of about 1°/min) and then held at that temperature for another thirty minutes. After the second heat treatment, the samples were cooled to room temperature by turning off the oven and opening the oven door. The salts were brushed from the samples after which they were washed and dried. The sample were then subjected to the biaxial flexure test. The results obtained are shown in Table I.

EXAMPLE V

The samples were prepared and treated in the same fashion as given in Example IV except that the initial slurry was prepared to give a 3:7 ratio of lithium:sodium ions. The samples were heated to a temperature of 750° C. and heat treated at that temperature for thirty minutes. The samples were cooled to 450° C. at which temperature they were held for a second heat treatment of thirty minutes. Results of the flexural testing are given in Table I.

EXAMPLE VI

This set of samples were prepared and treated according to the details given in Example IV except that the lithium salt mixture had a lithium:sodium ion ratio of 4:6. Results of flexural testing are given in TABLE I.

EXAMPLE VII

This set of samples were prepared and treated according to the details given in Example IV. The lithium/metal salt mixture was in a mole ratio of 1:9. and was prepared by mixing 2.12 g of lithium chloride (LiCl) and 26.30 g sodium chloride (NaCl) with 18 ml of distilled water to give a white slurry of syrupy consistency. Results of flexural testing are given in TABLE I.

EXAMPLE VIII

This set of samples were prepared and treated according to the details given in Example IV except that the lithium/ metal salt mixture was in a mole ratio of 1:3. Results of flexural testing are given in TABLE I.

EXAMPLE IX

This set of samples were prepared and treated according to the details given in Example IV except that the lithium/ metal salt mixture in a ratio of 1:19. Results of flexural testing are given in TABLE I.

EXAMPLE X

This set of samples were prepared and treated according to the details given in Example IV. The lithium/metal salt mixture was in a 1:9 mole ratio and prepared as detailed in Example VII. Results of flexural testing are given in TABLE I. In addition, a second set of discs were prepared and treated in the same fashion except that after the first heat treatment at 750° C. for thirty minutes, the discs were allowed to cool, the salt mixture was removed by washing with water, and the discs heated without the salt mixture to 450° C. where they were held for thirty minutes and then again cooled to room temperature. Results of flexural testing are given in TABLE I as Example X-A.

TABLE I

Lithium—Sodium Double Ion Exchange with High-Leucite Reinforced Dental Porcelain

| EXAMPLE | Li/Na Ratio | First Heat Treatment | Second Heat Treatment | Mean Flexural Strength (MPa) |
|---|---|---|---|---|
| I | (uncoated) | | | 94.8 ± 5.8 |
| II | (uncoated) | 750° C./30 min | 450°/30 min | 117.0 ± 11.0 |
| III | (Tuf-Coat) | 150° C./20 min | 450°/30 min | 131.1 ± 14.8 |
| IV | 1:1 | 750° C./30 min | 450°/30 min | 74.6 ± 12.1 |
| V | 3:7 | 750° C./30 min | 450°/30 min | 88.5 ± 20.2 |
| VI | 4:6 | 750° C./30 min | 450°/30 min | 93.1 ± 15.5 |
| VII | 1:9 | 650° C./30 min | 450°/30 min | 95.5 ± 12.5 |
| VIII | 1:3 | 750° C./30 min | 450°/30 min | 135.8 ± 24.5 |
| IX | 1:19 | 750° C./30 min | 450°/30 min | 156.7 ± 21.9 |
| X | 1:9 | 750° C./30 min | 450°/30 min | 170.4 ± 24.5 |
| X-A | 1:9 | 750° C./30 min | 450°/30 min | 149.1 ± 27.3 |

The results show that low lithium concentrations are more effective than high lithium concentrations in strengthening the surface layer. In part, this may be due to the fact the leucite reinforced material already contains about 2% $Li^+$ ion. Generally the first heat treatment at 750° C. (above the strain point) relates to the exchange of sodium and potassium ions in the porcelain for the lithium ions in the salt mixture. In the second heat treatment step at 450° (below the strain point), the lattice has contracted around the small lithium ions and has become "locked" into place as the ceramic cooled through the strain point. When the sodium ions in the salt mixture exchange with the lithium ions in the ceramic, their larger size forces the surface layer into a compressive state. The key to the surprising results obtained with the lithium ion exchange above the strain point of the ceramic is the deeper penetration (diffusion) of the ion into the ceramic. The final result of the dual ion-exchange was the formation of a thick compressive layer at the surface of the porcelain which resulted in an increase in flexural strength with low lithium concentrations. The results of the low temperature heat treatment without the salt mixture points out the additional strengthening effect obtained by the second heat treatment with the salt mixture in place as opposed to using the salt mixture in the first heat treatment only.

EXAMPLES XI THROUGH XVII

Seventy discs of low-leucite feldspathic dental porcelain (Ceramco II porcelain; Ceramco, Inc., E. Windsor, N.J.) 16 mm in diameter and 1.5 mm thick were prepared and tested according to the method noted above for Examples I to X except that a Ceramco II low-leucite (21.6%) ceramic (Si, 32.8%; Al, 5.7; Ca, 0.1; Na, 4.0; sodium, 4.7; potassium 5.7; and oxygen 50.6%) was used in conjunction with a lithium/potassium ion mixture. The ceramic discs were fired according to the manufacturer's schedule in an Ultra-Mat Model CDF furnace (Idle Temp, 538° C.; entry time, 6.0 minutes; Heating rate 42° C./min; Vacuum level 720 mm/Hg; High Temp., 938° C.; Hold Time, 2 min; Removal Time, 2.0 min). The specimens were randomly divided into seven groups (each group having a sample size of ten, i.e., n=10) and subjected to various treatments as indicated in Table II and in Examples XI through XVII. The mean flexural strength $\sigma_m$ was determined using the same method and procedure as detailed above for EXAMPLES I through X.

COMPARATIVE EXAMPLE XI

One set of discs was left untreated and subjected to the biaxial flexure test. The results obtained are shown in Table II.

COMPARATIVE EXAMPLE XII

A second set of discs was treated with Tuf-Coat according to the procedure set forth for Example III. The discs were tested for flexural strength according to the above set forth method. The results obtained are shown in Table II.

EXAMPLE XIII

A third set of discs was treated with a 1:3 lithium/potassium salt mixture according to the procedure set forth in Example IV except that reagent grade potassium chloride was substituted for sodium chloride. The high temperature heat treatment was carried out at 750° C. for fifteen minutes and the low temperature heat treatment was carried out at 450° C. for thirty minutes. The samples were then subjected to the biaxial flexure test. The results obtained are shown in Table II.

EXAMPLE XIV

The samples were prepared in the same fashion as given in Example XIII except that the high temperature heat treatment was carried out at 750° C. for thirty minutes Results of the flexural testing are given in Table II.

EXAMPLE XV

The samples were prepared and treated in the same fashion as given in Example XIII except that a lithium/potassium mole ratio of 1:1 was used. The high temperature heat treatment was carried out at 700° C. for thirty minutes. Results of the flexural testing are given in Table II.

EXAMPLE XVI

The samples were prepared and treated in the same fashion as given in Example XV except the samples were heat treated at 750° C. for thirty minutes and then cooled to 480° C. at which temperature they were held for a second heat treatment of thirty minutes. Results of the flexural testing are given in Table II.

EXAMPLE XVII

The samples were prepared in the same fashion as given in Example XVI except the second heat treatment was carried out at 450° C. for thirty minutes. Results of the flexural testing are given in Table II.

TABLE II

Lithium—Potassium Double Ion Exchange with Low-Leucite Reinforced Dental Porcelain

| EXAMPLE | Li/K Ratio | First Heat Treatment | Second Heat Treatment | Mean Flexural Strength (MPa) |
|---|---|---|---|---|
| XI | (uncoated) | 750° C./30 min | 450°/30 min | 60.7 ± 8.7 |
| XII | (Tuf-Coat) | 150° C./20 min | 450°/30 min | 81.3 ± 9.1 |
| XIII | 1:3 | 750° C./15 min | 450°/30 min | 68.2 ± 24.2 |
| XIV | 1:3 | 750° C./30 min | 450°/30 min | 73.3 ± 13.0 |
| XV | 1:1 | 700° C./30 min | 450°/30 min | 73.9 ± 5.5 |
| XVI | 1:1 | 750° C./30 min | 480°/30 min | 95.1 ± 26.5 |
| XVII | 1:1 | 750° C./30 min | 450°/30 min | 122.0 ± 10.8 |

As Table II shows, a one-step dual ion exchange significantly improved the strength of Ceramco II porcelain (low leucite porcelain) when used at a 1:1 Li/K ratio and a heat treatment of 30 minutes at 750° C. followed by another heat treatment at 450° C. for thirty minutes.

EXAMPLES XVIII THROUGH XXIV

Eighty discs of high-leucite feldspathic dental porcelain (OPTEC HSP; C 16 mm in diameter and 1.5 mm thick) were prepared according to the methods and treatments detailed for Examples I through X. The specimens were randomly divided into eight groups (each group having a sample size of ten, i.e., n=10) and subjected to various treatments as indicated in Table III and in Examples XVIII through XXV. The mean flexural strength was determined using the same method and procedure detailed above for EXAMPLES I through XVII. Samples XIX and XXII through XXV were first indented with a microhardness tester (9.81 to 78.4N) and then fractured in water with a ball-on-ring biaxial fixture at 0.5 mm/min with the treated side in tension. Wavelength Dispersive Spectrometry (WDS) analyses on cross-sections of the samples showed that the mean potassium amount in the glassy matrix was significantly lower for the treated specimens than for the controls to an average depth of 140 microns.

COMPARATIVE EXAMPLES XVIII and XIX

Two sets of discs was left untreated and subjected to the biaxial flexure test and WDS cross section analyses for the amount of potassium in the glassy matrix. One of the two sets (EXAMPLE XIX) was also subjected to microhardness testing. The results obtained are shown in Table III

COMPARATIVE EXAMPLE XX

A third set of discs was heat treated without ion exchange. The discs were subjected to flexural strength testing, potassium concentration analyses through the cross section, and microhardness testing according to the above set forth methods. The results obtained are shown in Table III.

EXAMPLES XXI THROUGH XXIV

Each of the sets of discs for Examples XXI through XXIV were dual ion exchanged at 750° C. and 450° C. with a mixture of lithium and sodium salts in a 1:9 mole ratio. The samples were tested for microhardness and flexural strength according to the methods noted above. Cross sectional analysis for potassium was carried out using wavelength dispersive spectrometry. Results of the flexural and microhardness testing are given in Table III.

TABLE III

Lithium—Potassium Double Ion Exchange with High-Leucite Reinforced Dental Porcelain Flexural Strength and Microhardness

| EXAMPLE | Treatment | Treatment Temperatures | Indentation Load (N) | Mean Flexural Strength (MPa) |
|---|---|---|---|---|
| XIII | none | none | 0.0 | 90.0 ± 6.1 |
| XIX | none | none | 9.8 | 63.7 ± 11.8 |
| XX | none | 750° C.–450° C. | 0.0 | 114.8 ± 10.8 |
| XXI | dual ion | 750° C.–450° C. | 0.0 | 175.2 ± 29.2 |
| XXII | dual ion | 750° C.–450° C. | 9.8 | 173.1 ± 14.8 |
| XXIII | dual ion | 750° C.–450° C. | 29.4 | 148.9 ± 25.4 |
| XXIV | dual ion | 750° C.–450° C. | 49.1 | 140.9 ± 28.4 |
| XV | dual ion | 750° C.–450° C. | 78.5 | 75.8 ± 22.8 |

It is possible that changes in configurations to other than those shown could be used but that which is shown if preferred and typical. Without departing from the spirit of this invention, various means of mixing, heating, and cooling the various compositions may be used.

It is therefore understood that although the present invention has been specifically disclosed with the preferred embodiment and examples, modifications to the design concerning mixing, heating, cooling, and other aspects of sample manipulation will be apparent to those skilled in the art and such modifications and variations are considered to be equivalent to and within the scope of the disclosed invention and the appended claims.

We claim:

1. A method of strengthening the surface of a dental ceramic restorative material comprising:
   a. a depositing step comprising depositing a mixture of an inorganic lithium salt and an inorganic salt with a metal ion larger than a lithium ion on the surface of a dental ceramic restorative material;
   b. a first heat treating step comprising heat treating said dental ceramic material having said mixture thereon at a temperature above the strain temperature of said ceramic material; and
   c. a second heat treating step comprising heat treating said ceramic material at a temperature below the strain temperature of said ceramic material with a mixture of an inorganic lithium salt and an inorganic metal salt with the metal ion of said inorganic metal salt being larger than said lithium ion after said first heat treating step.

2. The method according to claim 1 wherein said second heat treating step is carried out with said mixture from said first heating step thereon.

3. The method according to claim 1 with said ceramic material being an aluminosilicate.

4. The method according to claim 3 wherein said aluminosilicate is a porcelain.

5. The method according to claim 4 wherein said porcelain is a feldspathic porcelain.

6. The method according to claim 5 wherein said feldspathic porcelain contains leucite.

7. The method according to claim 6 wherein said feldspathic porcelain contains at least about thirty weight percent leucite.

8. The method according to claim 1 wherein said metal ion of said inorganic metal salt that is larger than said lithium ion is an alkali metal ion.

9. The method according to claim 8 wherein said metal ion of said inorganic metal salt that is larger than said lithium ion is selected from the group of alkali metal ions consisting of sodium, potassium, rubidium, and cesium.

10. The method according to claim 9 wherein said metal ion of said inorganic metal salt that is larger than said lithium ion is sodium.

11. The method according to claim 9 wherein said metal ion of said inorganic metal salt that is larger than said lithium ion is potassium.

12. The method according to claim 1 wherein said first heat treating step is carried out at a temperature above at least about 100° C. above said strain temperature.

13. The method according to claim 12 wherein said first heat treating step is carried out at a temperature above about 200° C. above said strain temperature.

14. The method according to claim 1 wherein said second heat treating step is carried out at a temperature below at least about 50° C. below said strain temperature.

15. The method according to claim 14 wherein said second heat treating step is carried out at a temperature below about 100° C. below said strain temperature.

16. The dental ceramic with a strengthened surface layer obtained according to the method of claim 1.

17. A method of strengthening the surface layer of a dental ceramic restorative material comprising:
   a. depositing a mixture of an inorganic lithium salt and an inorganic metal salt having a metal ion with an ionic crystal radius larger than the ionic crystal radius of a lithium ion on the surface of said dental ceramic material;
   b. heating said ceramic material having said mixture thereon to a temperature above the strain temperature of said dental ceramic material;
   c. heat treating said ceramic material having said mixture thereon at a temperature above the strain temperature of said ceramic material;
   d. lowering the temperature of said ceramic material having a resultant mixture from said heating treating step carried out at above said strain temperature thereon to a temperature below said strain temperature;
   e. heat treating said ceramic material at a temperature below said strain temperature with said resultant mixture from said heating treating step carried out at above said strain temperature thereon; and
   f. cooling said ceramic restorative material with a resulting mixture to ambient temperature.

18. The method according to claim 17 wherein said dental ceramic restorative material is a porcelain.

19. The method according to claim 18 wherein said porcelain is a feldspathic porcelain.

20. The method according to claim 19 wherein said porcelain is a feldspathic porcelain containing leucite.

21. The method according to claim 20 with said feldspathic porcelain containing at least about thirty weight percent leucite.

22. The method according to claim 17 wherein said metal ion with an ionic crystal radius larger than the ionic crystal radius of said lithium ion is an alkali metal ion.

23. The method according to claim 22 wherein said alkali metal ion with an ionic crystal radius larger than the ionic crystal radius of said lithium ion is a sodium ion.

24. The method according to claim 22 wherein said alkali metal ion with an ionic crystal radius larger than the ionic crystal radius of said lithium ion is a potassium ion.

25. The dental ceramic with a strengthened surface layer obtained according to the method of claim 17.

* * * * *

UNITED STATES PATENT AND TRADEMARK OFFICE
CERTIFICATE OF CORRECTION

PATENT NO. : 5,705,273
DATED : January 6, 1998
INVENTOR(S) : Denry et al.

It is certified that error appears in the above-indentified patent and that said Letters Patent is hereby corrected as shown below:

Column 1, line 3, insert the following before BACKGROUND OF INVENTION:

STATEMENT REGARDING FEDERALLY SPONSORED RESEARCH

The U.S. Government has a paid-up license in this invention and the right in limited circumstances to require the patent owner to license others on reasonable terms as provided for by the terms of Grant No. R01-DE09119 awarded by the National Institute of Health/National Institute of Dental Research.

Column 3, line 6, delete "stain" and insert therefor - - strain - -.

Column 4, line 5, delete "addition" and insert therefor - - additional - -.

Column 8, line 1, after "treatment" delete ")";

line 53, delete "ration" and insert therefor - - ratio - -.

Column 11, line 7, delete "Na, 4.0;".

Column 12, line 25, delete "XXIV" and insert therefor - - XXV - -;

line 60, delete "XXIV" and insert therefor - - XXV - -;

line 62, delete "XXIV" and insert therefor - - XXV - -.

Column 13, line 19, delete "XV" and insert therefor - - XXV - -;

UNITED STATES PATENT AND TRADEMARK OFFICE
CERTIFICATE OF CORRECTION

PATENT NO. : 5,705,273
DATED : January 6, 1998
INVENTOR(S) : Denry, et al

It is certified that error appears in the above-indentified patent and that said Letters Patent is hereby corrected as shown below:

Column 13, line 22, after "is shown" delete "if" and insert therefor --is--.

Signed and Sealed this

Twenty-third Day of June, 1998

Attest:

BRUCE LEHMAN

*Attesting Officer*    *Commissioner of Patents and Trademarks*